United States Patent
Pandey et al.

(10) Patent No.: US 9,872,903 B2
(45) Date of Patent: Jan. 23, 2018

(54) TARGETING THYMIDINE KINASE PHOTOSENSITIZER AND PHARMACEUTICAL COMPOSITION AND USE FOR CANCER TREATMENT THEREOF

(71) Applicant: ZHEJIANG HISUN PHARMACEUTICAL CO., LTD., Taizhou, Zhejiang (CN)

(72) Inventors: Ravindra K Pandey, East Amherst, NY (US); Yihui Chen, Amherst, NY (US); Hua Bai, Taizhou (CN); Zhenliang Chen, Taizhou (CN)

(73) Assignee: ZHEJIANG HISUN PHARMACEUTICAL CO., LTD, Taizhou (CN)

( * ) Notice: Subject to any disclaimer, the term of this patent is extended or adjusted under 35 U.S.C. 154(b) by 322 days.

(21) Appl. No.: 14/434,102

(22) PCT Filed: Nov. 2, 2012

(86) PCT No.: PCT/CN2012/083977
§ 371 (c)(1),
(2) Date: Oct. 16, 2015

(87) PCT Pub. No.: WO2014/056270
PCT Pub. Date: Apr. 17, 2014

(65) Prior Publication Data
US 2016/0151494 A1    Jun. 2, 2016

(30) Foreign Application Priority Data
Oct. 8, 2012 (CN) .......................... 2012 1 0394006

(51) Int. Cl.
| | |
|---|---|
| *A01N 43/04* | (2006.01) |
| *A61K 31/70* | (2006.01) |
| *A61K 41/00* | (2006.01) |
| *C07D 487/22* | (2006.01) |
| *A61K 47/48* | (2006.01) |
| *A61K 49/00* | (2006.01) |
| *A61K 31/7072* | (2006.01) |
| *A61K 31/337* | (2006.01) |
| *A61K 31/7064* | (2006.01) |
| *A61K 31/7068* | (2006.01) |
| *A61K 31/706* | (2006.01) |

(52) U.S. Cl.
CPC ........ *A61K 41/0057* (2013.01); *A61K 31/337* (2013.01); *A61K 31/7072* (2013.01); *A61K 41/0071* (2013.01); *A61K 47/48061* (2013.01); *A61K 47/48092* (2013.01); *A61K 49/0036* (2013.01); *C07D 487/22* (2013.01); *A61K 31/706* (2013.01); *A61K 31/7064* (2013.01); *A61K 31/7068* (2013.01)

(58) Field of Classification Search
None
See application file for complete search history.

(56) References Cited

U.S. PATENT DOCUMENTS

| | | | |
|---|---|---|---|
| 5,198,460 A | * | 3/1993 | Pandey .............. A61K 51/0485 514/410 |
| RE38,994 E | | 2/2006 | Pandey et al. |
| RE39,094 E | | 5/2006 | Pandey et al. |

OTHER PUBLICATIONS

International Search Report dated Jul. 18, 2013 for PCT/CN2012/083977.
Translation of International Search Report dated Jul. 18, 2013 for PCT/CN2012/083977.
Rolf Muschter, Photodynamic Therapy: A New Approach to Prostate Cancer, Current Eurology Reports 2003, 4:221-228.
Zaak, Dirk et al., Photodynamic Therapy by Means of 5-ALA Induced PPIX in Human Prostate Cancer—Preliminary Results, Med. Laser Appl. 18: 91-95 (2003).
R. Alex Hsi et al., Photodynamic Therapy in the Canine Prostate Using Motexafin Lutetium, Clinical Cancer Research, vol. 7 pp. 651-660, Mar. 2001.
Dougherty, Thomas J. et al., Photoradiation Therapy fo rthe Treatment of Malignant Tumors, Cancer reserach 38, pp. 2628-2635, Aug. 1978.

* cited by examiner

*Primary Examiner* — Patrick T Lewis
(74) *Attorney, Agent, or Firm* — Zareefa B. Flener; Flener IP & Business Law

(57) ABSTRACT

A targeting thymidine kinase photosensitizer and pharmaceutical composition and use for cancer treatment thereof is provided, which improves the selectivity of photosensitizers to tumor cells, has better tolerance, can reach maximum blood concentration in 24 hours, has a bigger conjugated system, a longer absorption wavelength and an advantage in treating depth tumors; the wavelength area does not need to consume much energy of a light-output device and even LEDs can be used, which render PDT more practical and economical. The targeting thymidine kinase photosensitizer can be used for diagnosis and for treating prostatic carcinoma via the guidance of fluorescence imaging. The pharmaceutical composition uses a combination of a chemotherapeutic agent and the targeting thymidine kinase photosensitizer, which further improves the therapeutic effect of the PDT method, expands the application range for tumors and has good effects on metastatic tumors as well.

18 Claims, 4 Drawing Sheets

TARGETING THYMIDINE KINASE PHOTOSENSITIZER AND PHARMACEUTICAL COMPOSITION AND USE FOR CANCER TREATMENT THEREOF

The present application claims the priority of Chinese patent application No. 201210394006.2, filed on 10, Oct., 2012, to the Patent Office of the People's Republic of China, and titled "Targeting thymidine kinase photosensitizer and pharmaceutical composition and use for cancer treatment thereof", which is hereby incorporated by reference in its entirety.

FIELD OF THE INVENTION

The present invention relates to the pharmaceutical field, and particularly to a targeting thymidine kinase photosensitizer and pharmaceutical composition and use for cancer treatment thereof.

BACKGROUND OF THE INVENTION

Prostatic cancer is the most common non-skin infectious malignant tumors, and is the second leading cause of death in males, second to lung cancer. In United States, near 190 thousand of people are diagnosed as suffering prostatic cancer each year, in which approximately 31 thousand of people die from it. Prostatic cancer is a multifocal disease, so that the whole gland should be managed and treated. At present, the treatment methods mainly include observation only (intimate observation and wait), operation (radical prostatectomy), radiation (external irradiation or brachytherapy using an implanted radioactive source), radiation together with hormonotherapy (new adjuvant therapy) and hormone therapy (androgen-blocking therapy). Furthermore, it has been reported that cryotherapy, chemotherapy and other novel methods are also used for a local lesion by some doctors. Unfortunately, however, there are some disadvantages in all these methods, so that novel treatment methods are urgently demanded for prostatic cancer.

It has been demonstrated by clinical studies that photodynamics therapy (PDT) is an attractive form for cancer treatment, the principle of which includes: a photosensitizer is selectively absorbed by the tumor tissue and stored inside, and subsequently the photosensitizer is activated under local irradiation using the light at an appropriate wavelength, so that photosensitive effect is created. There will not be severe systemic side effect resulted from PDT, and it can be used repeatedly. PDT will not affect the tissue cells around when it destroys the tumor cells. There are 3 prominent advantages of PDT, including: favorable acceptability, low side effect and high efficiency.

At the end of 1970s and the early of 1990s, many attempts have been made by scientists to obtain a photosensitizer-PDT for prostatic cancer, so that the tissue-based photosensitizer has been developed. Meanwhile, novel PDT-mediated photosensitizer appears to have a great potential for the treatment of prostatic cancer (Photodynamic Therapy: A New Approach to Prostate Cancer. *Curr. Urol. Rep.* 2003, 4, 221-228). It has been proved by the University College London (London, UK) that there was a potential therapeutic effect of temoporfin for the treatment of prostatic cancer. Zaak and his colleagues reported the use of aminolevulinic acid-mediated protoporphyrin IX for the treatment of prostatic cancer (Photodynamic therapy by means of 5-ALA induced PPIX in human prostate cancer—preliminary results. *Medical Laser Application* 2003, 18, 91-95). Motexafin lutetium is a remarkable vessel activating photosensitizer, and has been tested in dog model (Photodynamic therapy in the canine prostate using motexafin lutetium. *Clin Cancer Res* 2001, 7, 651-660), Motexafin lutetium has also been applied to the patient after radiotherapy. It has been reported that it is better to use high dose PDT than low dose PDT. Padoporfin (Tookad®) and padeliporfin (Stakel®) are palladium-bacteriopheophorbide photosensitizer. On the first test stage of Padoporfin, 28 Canada patients suffered from periodic prostate cancer were enrolled for radiotherapy. It has been indicated that the pharmacuetical dosage of 2 mg/kg has the best therapeutic effect. Subsequently, the effect of using padeliporfin in the treatment of prostatic cancer of male patients without radiotherapy is also quite favorable. In conclusion, since the first use of photodynamics therapy for the treatment of prostatic cancer in 1978 (Photoradiation Therapy for the Treatment of Malignant Tumors. Cancer Res. 1978, 38, 2628-2635), and with the significant development of light transmission and photosensitizer design, many photosensitizers can be finally evaluated in formal clinical trials.

Although many photosensitizers have been developed in recent years and some were tested in clinical trials, such as Tookad and m-THPC, there are inherent disadvantages in these two analogues. For example, although no obvious skin phototoxicity induced by Tookad after long wavelength irradiation is observed, the therapeutic effect is not completely the same for all the patients, since the infusion and light process almost occur at the same time due to very short time span from the injection to the light process (i.e., very short effective treatment window). Additionally, after the injection of m-THPC, the medicine concentration will be adequate to kill tumor cells after a long period (3-4 days) of blood circulation; furthermore, it will also have severe skin phototoxicity.

There is another type of well-tested photosensitizer of tetrapyrrole or reduced tetrapyrrole structure, 2-((1'-n-hexyloxy)ethyl)-2-devinyl-pyropheophorbide-α (HPPH) and the analogues thereof, wherein the HPPH has the following structure:

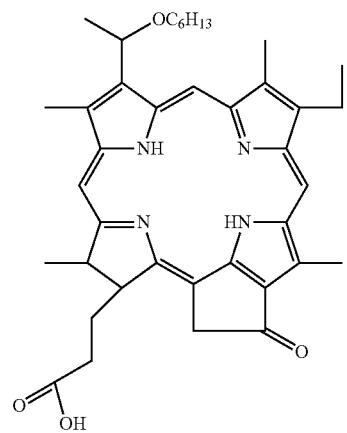

The preparation method of HPPH and the salts thereof can be found in U.S. Pat. No. 5,198,460 (Publication No. RE39094) and U.S. Pat. No. 5,314,905 (Publication No. RE38994) or the following article: Methyl Pyropheophorbide-a Analogs: Potential Fluorescent Probes for the Peripheral-Type Benzodiazepine Receptor. Effect of Central Metal in Photosensitizing Efficacy. J. Med. Chem (rapid communication). 2005, 48 (11), 3692-3695. The phototoxicity duration of HPPH is much shorter than that of other photosensitizers, and HPPH has less damage to normal tissues with better therapeutic effect. However, erythema and other injuries will still be induced when tumor and other hyperplastic tissues are treated.

In another aspect, the key point in the use of photosensitizer-PDT therapy for the treatment of prostatic cancer is to enhance the selectivity of PDT photosensitive reagent to prostatic cancer cells. At present, in many cancer imaging and treatment methods, proliferation of tumor cells and DNA synthesis are utilized. The synthesis of deoxyribonucleic acid (DNA) occurs at a special stage—S phase in cell cycle. A great amount of DNA is synthesized during tumor cell proliferation, while thymidine kinase 1 has higher activity in hyperplastic cells, which is regulated by cells of S phase. Accordingly, the cell proliferation can be investigated by comparing the DNA synthesis of cells of stationary phase and hyperplastic cells of S phase in cell cycle via labeled thymidine. Early in laboratory, thymidine was labeled by 3H and 14C, and subsequently, 11C-thymidine was synthesized using positron emission tomography (PET). Pyrimidine is the basic unit for DNA synthesis, so that the use of 11C-thymidine for imaging is of great significance. Although this method is suitable for survey and effectiveness investigation, it is still not well acceptable due to excessively short half life of 11C. Since the half life of 11C-thymidine is very short and it may be degraded rapidly, the regular clinical application is not practical. As a result, efforts have been continuously made to find thymidine analogs with better imaging performance.

Thymidine analogs have been widely investigated as a possible therapeutic compound in both pharmaceutical industry and academic field. These analogs have been initially investigated by Dr. Charles Heidelberg. He tried to find a thymidine analog that can interfere the synthesis of DNA, and 5-fluorouracil was finally developed in 1975. 5-fluorouracil is a very effective antineoplastic drug, and still extensively employed in clinical treatment. When the thymidine analog $^{18}$F-FLT enters inside of the body, it can be absorbed by cells and aggregated after phosphorylation by thymidine kinase 1. It has been found that 3'-deoxy-3'-fluorothymidine (FLT) can be labeled by $^{18}$F ($^{18}$FLT), an isotope with longer half-life (109.8 min). By evaluation of the performance of many nucleoside analogs for the imaging of hyperplasia, $^{18}$F-FLT (3'-deoxy-3'-fluorothymidine) is still the best method by far.

Furthermore, when prostatic cancer is treated by photosensitizer-PDT therapy, the whole prostate is demanded to be exposed under illumination at appropriate wavelength (based on the photosensitizer used). In addition, although photosensitizer-PDT therapy is very effective for cancer treatment, it only can be used for local treatment, i.e., for primary tumor, and it has limited application in the treatment of metastatic tumor. For metastatic tumors, chemotherapeutic agents are commonly needed, such as paclitaxel, which has systemic effectiveness. Accordingly, it is limited, at present, to use photosensitizer-PDT therapy or chemotherapy alone for the treatment of prostatic cancer, which has undesirable effect.

SUMMARY OF THE INVENTION

Based on the content mentioned above, the present invention provides a targeting thymidine kinase photosensitizer with better therapeutic effect and imaging performance, and also provides the pharmaceutical composition of the targeting thymidine kinase photosensitizer and the use for the treatment of cancers thereof.

The technical solution used in the present invention is as follows:

In one aspect, the present invention relates to a targeting thymidine kinase photo sensitizer, which has the structure of Formula I:

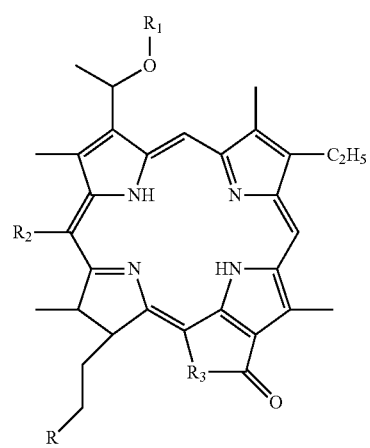

wherein, —R is —COO—$R_5$ or —CO—NH—$R_5$,

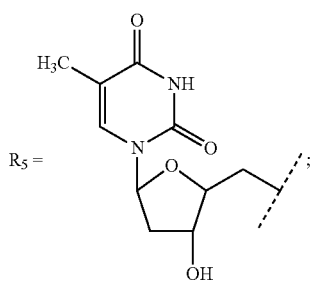

$R_1$ is alkyl;
$R_2$ is H or phenyl substituted by R at para-position, and the substituent R is defined as above;
—$R_3$ is —$CH_2$ or —CO—$NR_4$, and its carbonyl end is attached to the carbon atom of the carbon-carbon double-bond on the mother nucleus of the photosensitizer, and $R_4$ is alkyl.

The photosensitizer of the present invention is formed by conjugation between conventional photosensitizer of tetrapyrrole or reduced tetrapyrrole structure and thymidine, and is an enhanced photosensitizer with larger conjugate system. The mode of conjugation can be in the form of ester bond or amido bond, and it is named as targeting thymidine kinase photosensitizer due to the thymidine structure.

Furthermore, in some Examples, —R is —COO—$R_5$.
Furthermore, in some Examples, $R_1$ is n-butyl or n-hexyl.
Furthermore, in some Examples, —$R_3$ is —$CH_2$ or —CO—$NR_4$, and its carbonyl end is attached to the carbon atom of the carbon-carbon double-bond on the mother nucleus of the photosensitizer, and $R_4$ is n-butyl or n-hexyl.
Furthermore, in some Examples, the structure of the targeting thymidine kinase photosensitizer is as shown in Formula II, Formula III, or Formula IV:

II

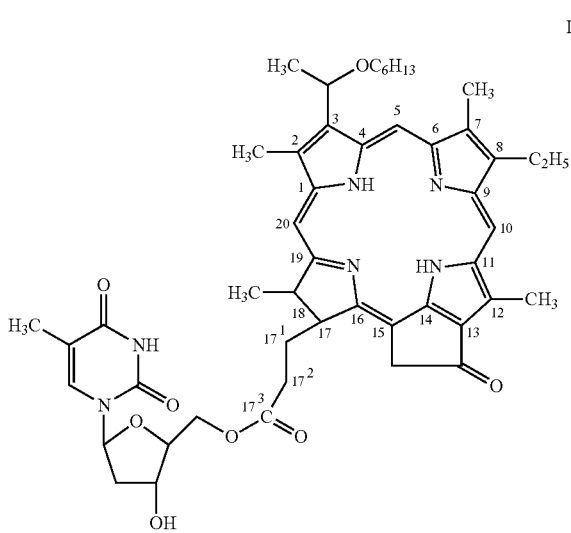

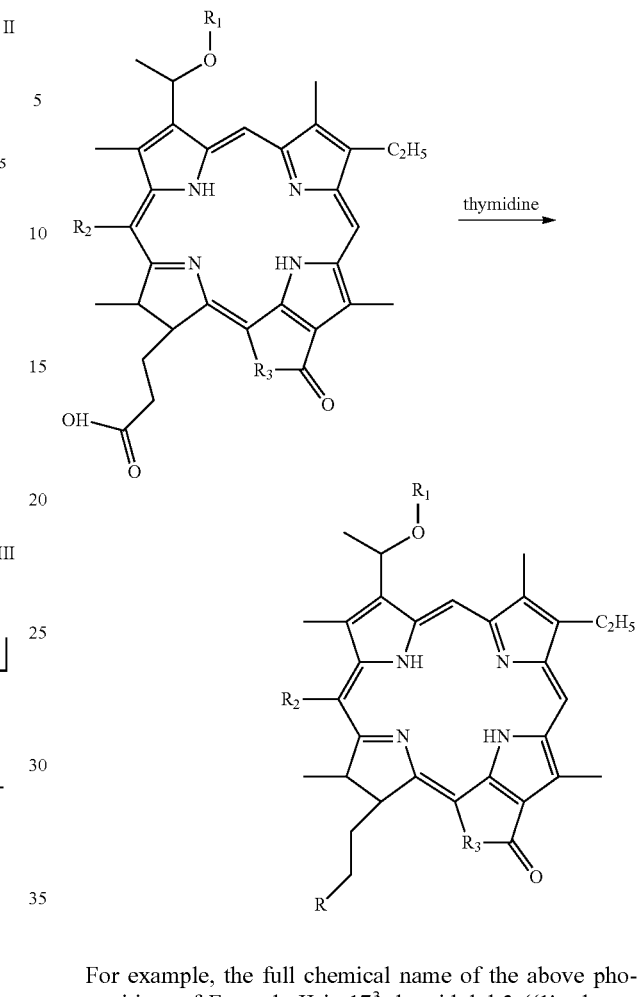

III

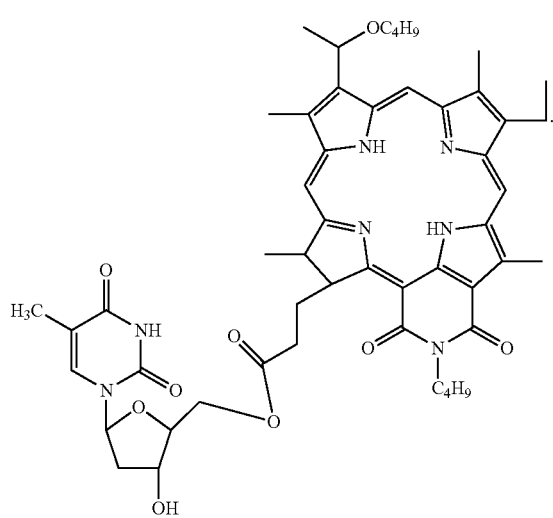

IV

The targeting thymidine kinase photosensitizer wherein R is —COO—$R_5$ and $R_2$ is H can be prepared using HPPH or analogs thereof as the starting material, and by direct conjugation through esterification with thymidine, the specific route is as follows:

For example, the full chemical name of the above photosensitizer of Formula II is $17^3$-thymidylyl-3-((1'-n-hexyloxy)ethyl)-3-devinyl-pyropheophorbide, which is prepared by the formation of an ester bond through condensation between the carboxy group of HPPH and the hydroxy group of thymidine, and it is thus also named as HPPH-thymidine conjugate. The preparation method of the photosensitizer is as follows: HPPH, Carter condensation agent, thymidine and triethylamine are dissolved in anhydrous dimethyl formamide (DMF), and reacted over night by stirring.

Wherein the Carter condensation agent is benzotriazol-1-yl-oxytris(dimethylamino)-phosphonium hexafluorophosphate (BOP), which is commercially available. Thymidine can be purchased from Aldrich, Sigma and BDH etc. Since the hydroxy group on the thymidine can be converted into amino group under certain conditions, i.e.,

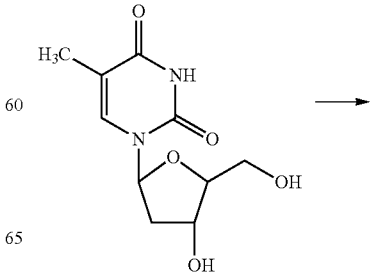

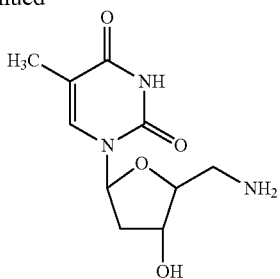

The HPPH above can be conjugated to thymidine by amido bond to prepare the targeting thymidine kinase photosensitizer of the present invention.

Additionally, the compound of Formula IV can also be prepared using HPPH or the analogs thereof as the starting material and by direct conjugation with thymidine, which is as follows:

As mentioned in Background, the starting material HPPH or the analogs thereof have already been sufficiently tested, and their preparation methods, and especially the preparation method of HPPH, are sufficiently disclosed. The preparation method for compound 7 in the Figure above can be found in the following article: Synthesis, Photophysical Properties, Tumor Uptake, and Preliminary in Vivo Photosensitizing Efficacy of a Homologous Series of 3-(1'-Alkyloxy)ethyl-3-devinylpurpurin-18-N-alkylimides with Variable Lipophilicity (Journal of Medicinal Chemistry, 2001, vol. 44, #10 p. 1540-1559).

The targeting thymidine kinase photosensitizer wherein R is —COO—$R_5$ and $R_2$ is phenyl substituted by R at para-position can be prepared using HPPH or the analogs thereof as the starting material, and initially by a series of reactions including halogenation etc., and subsequently by direct conjugation with thymidine. The synthetic route is as follows (X is halogen atom, such as Br, in the Figure):

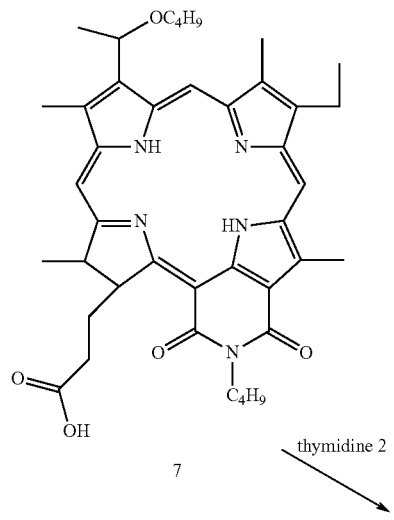

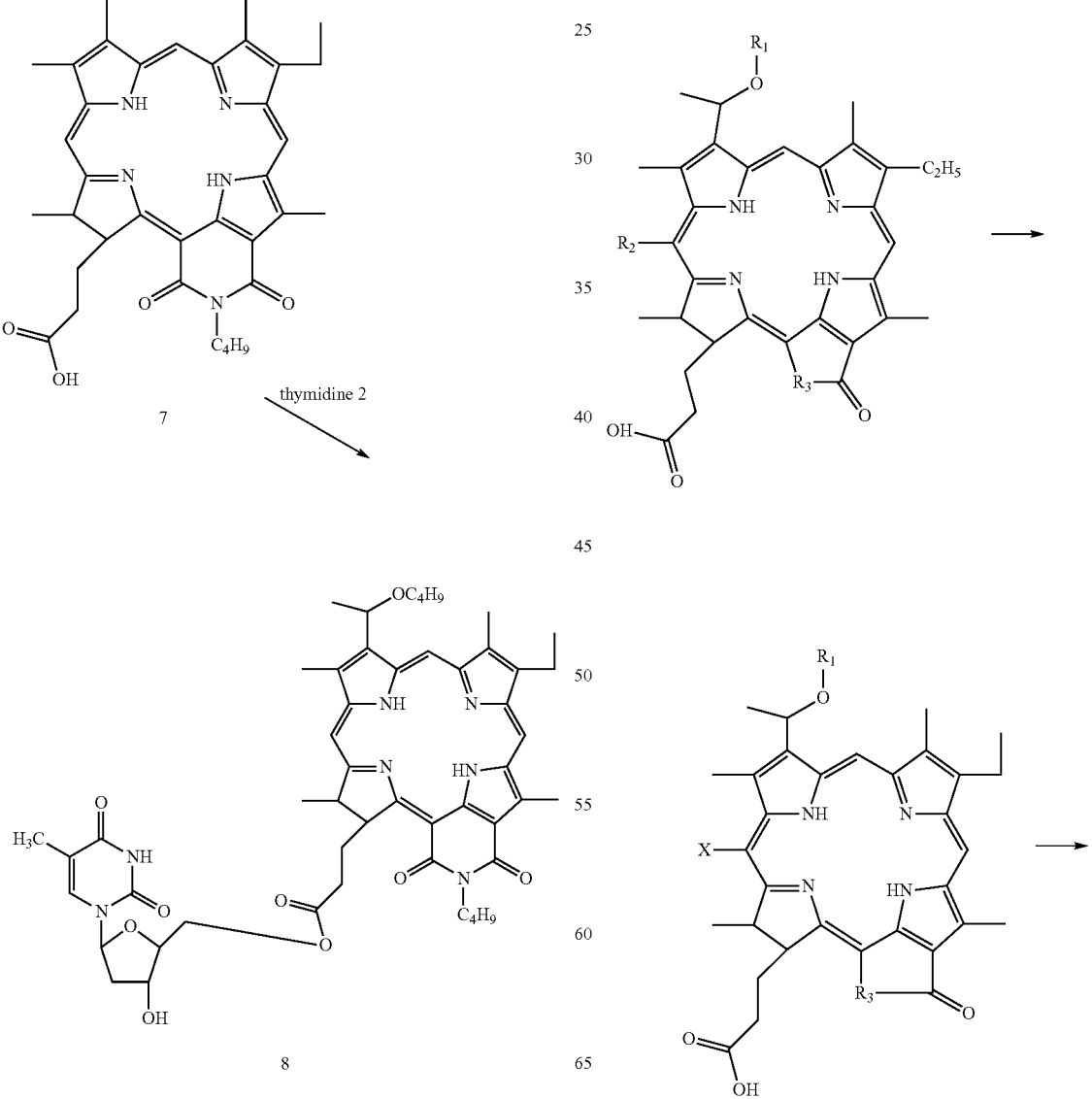

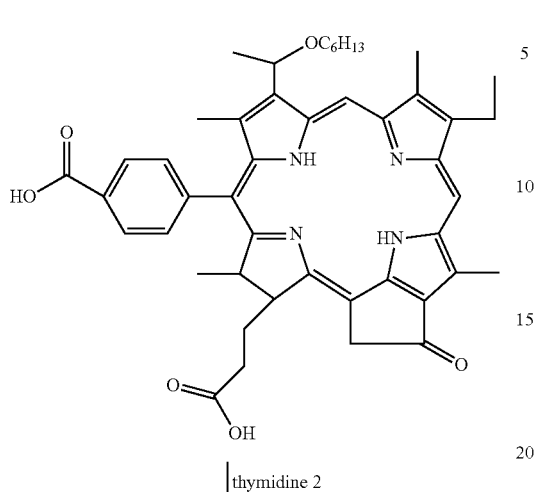
5
↓ thymidine 2
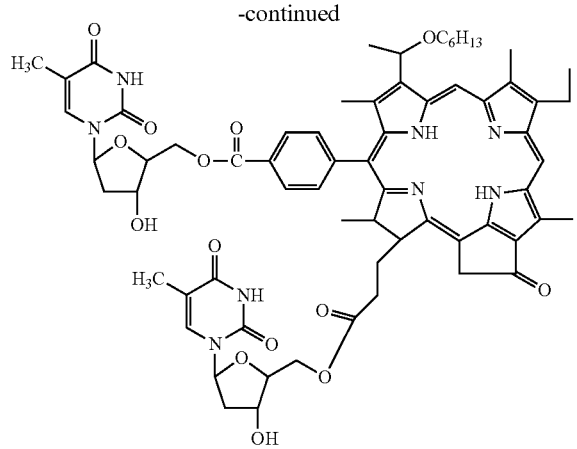
For example, the compound of Formula III (i.e., compound 6 in the Figure below) can be prepared using HPPH (i.e., compound 1 in the Figure below) as starting material, and initially by reaction with pyridinium tribromide, and subsequently by direct conjugation with thymidine. The synthetic route is as follows:
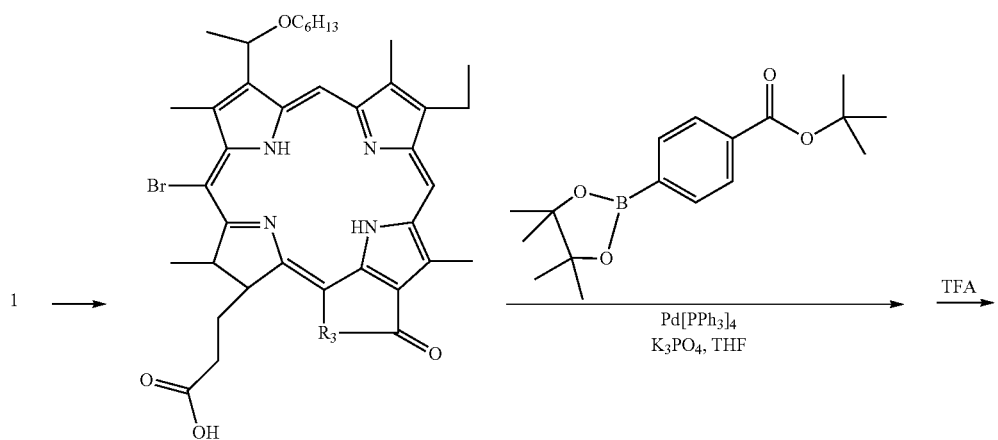
4
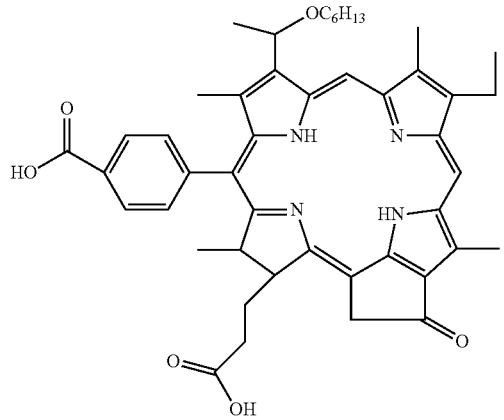
5
↓ thymidine 2

-continued

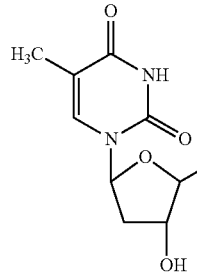
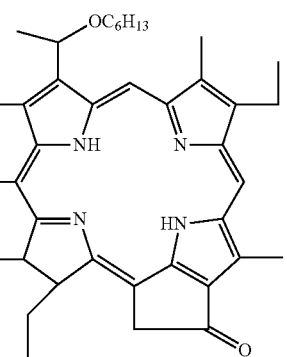
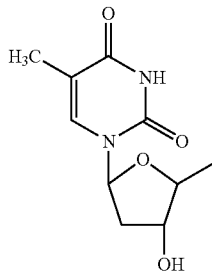

6

In the present invention, it has been demonstrated by fluorescence imaging test that the targeting thymidine kinase photosensitizer of the present invention has excellent imaging performance, and thus can be helpful for the imaging guidance treatment of prostatic cancer and other cancers. Accordingly, the present invention further provides the use of photosensitizer in the preparation of pharmaceuticals for the treatment of prostatic cancer and other cancers via the guidance of fluorescence imaging.

Furthermore, in another aspect, the present invention relates to a pharmaceutical composition, which includes the targeting thymidine kinase photosensitizer described herein and a chemotherapeutic agent.

Furthermore, in some Examples, the chemotherapeutic agent is paclitaxel.

In the present invention, it has been demonstrated by the comparative experiment of PDT therapeutic effect that the therapeutic effect of PDT has been enhanced by the use of photosensitizer HPPH-thymidine conjugate described herein in combination with paclitaxel. Accordingly, the invention also provides the use of the pharmaceutical composition in the preparation of pharmaceuticals for the treatment of primary prostatic cancer, other primary tumors and metastatic tumors via the guidance of fluorescence imaging.

As compared with the prior art, the targeting thymidine kinase photosensitizer described herein has the following advantages:

1. The selectivity of the photosensitizer on tumor cells is enhanced by the targeting thymidine kinase photosensitizer described herein, which allows the in vivo curative ratio of tumor to be enhanced from 30% of HPPH to 50% of HPPH-thymidine conjugate. PDT photosensitizer of the invention does not has excessively short treatment window as Tookad, and also eliminates the long-term skin phototoxicity of m-THPC, which has the disadvantage that 3-4 days are demanded for aggregation at tumor cells. The targeting thymidine kinase photosensitizer of the invention has better tolerance, and is able to achieve its maximum blood concentration at 24 h;

2. The targeting thymidine kinase photosensitizer described herein has larger conjugate system and longer absorbing wavelength, which is favorable for the treatment of depth tumors; for this region of wavelength, it doesn't need to consume a lot of energy of the light output device, and even an LED can be used, which makes PDT more practical and economic;

3. The chemotherapeutic agent is used in combination with the targeting thymidine kinase photosensitizer in the pharmaceutical composition described herein, which further increases the therapeutic effect of PDT, and for example, the tumor curative ratio has been enhanced from 50% of HPPH-thymidine conjugate used alone to 70% of the conjugate used in combination with paclitaxel;

4. The targeting thymidine kinase photosensitizer described herein not only can be used for diagnose, but also can be used for the treatment of prostatic cancer via the guidance of fluorescence imaging, which truly makes "see and treat" realized; when further used in combination with a chemotherapeutic agent as a pharmaceutical composition, the scope of cancers that can be treated is enlarged, which exhibits excellent therapeutic effect on metastatic tumor as well.

DETAILED EMBODIMENTS

The present invention will be further described by reference to the Figures and Examples below.

Example 1: Preparation of HPPH-Thymidine Conjugate

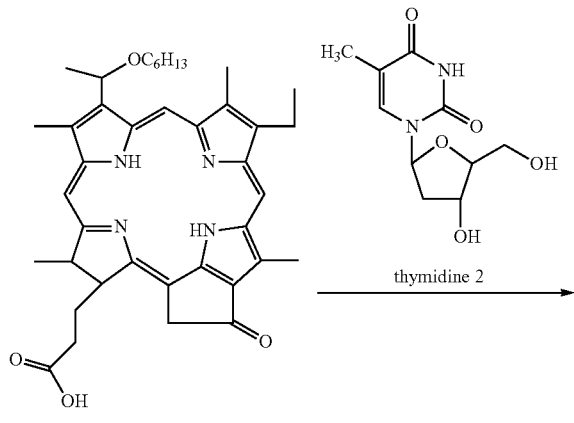

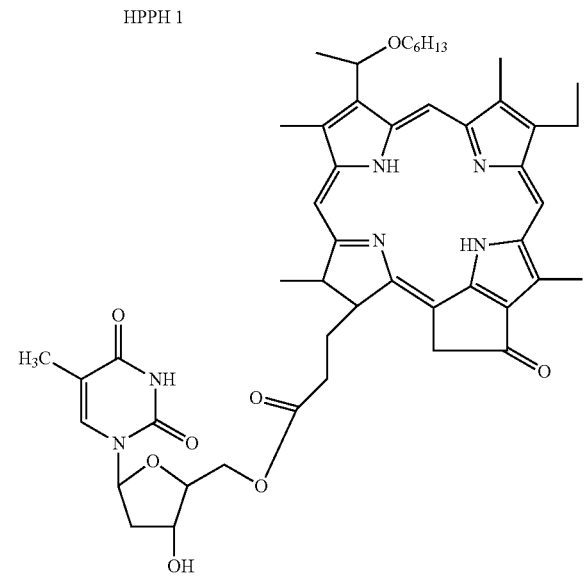

Figure 1:
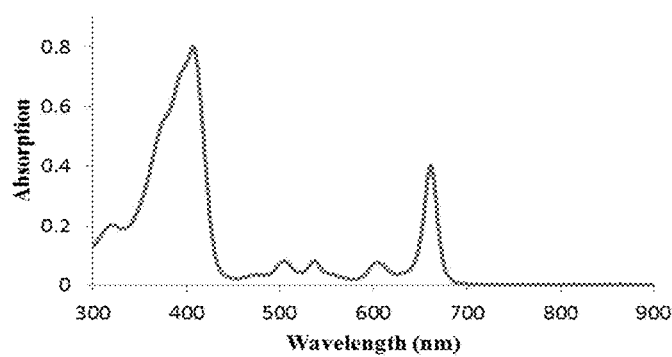
FIG. 1 is the electronic absorption spectroscopy of the HPPH-thymidine conjugate of Example 1 in the present invention, which is plotted with wavelength as X axis (expressed in nm), and absorption strength as Y axis.

HPPH was numbered as Compound 1, and HPPH-thymidine conjugate was numbered as Compound 3; specific preparation method was as follows:

HPPH (300 mg, 0.48 mmol), benzotriazol-1-yl-oxytris (dimethylamino)-phosphonium hexafluorophosphate (255 mg, 0.58 mmol), thymidine (1800 mg, 7.2 mmol) and triethylamine (about 0.5 mL) were dissolved in about 20 mL anhydrous dimethyl formamide (DMF) and reacted over night by stirring. After removal of DMF under vacuum, the mixture was purified by chromatography using 15% MeOH/CH$_2$Cl$_2$ as the eluent to give the target product with yield of more than 52% (210 mg), and its electronic absorption spectroscopy was shown in FIG. 1 (ultraviolet-visible light, and the methanol concentration of 7.7 µM), $\lambda_{max}$ (MeOH), nm (ε): 663 nm (5.25×10$^4$), 606 nm (7.49×10$^3$), 538 nm (7.51×10$^3$), 507 nm (7.28×10$^3$), 412 nm (10.52×10$^4$).

Figure 2:
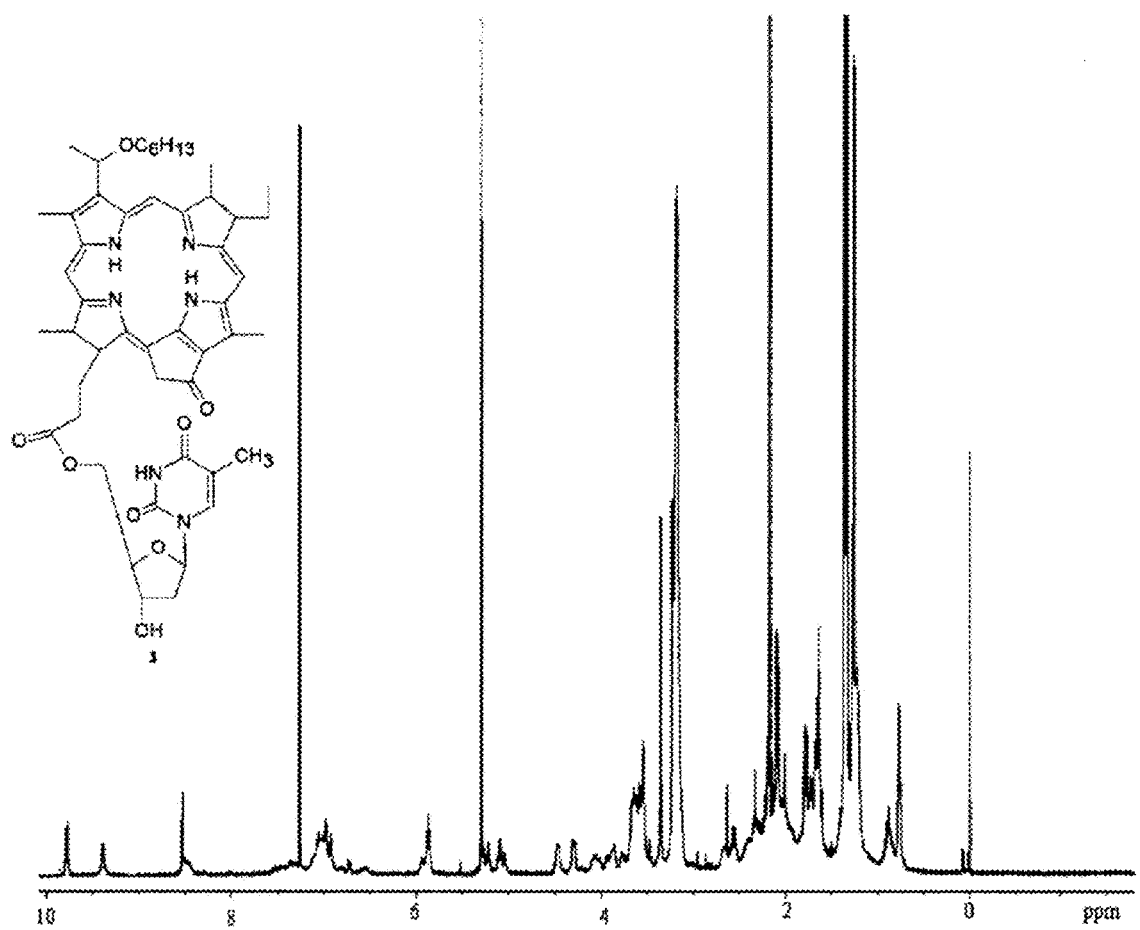
FIG. 2 is a 1H-NMR graph of the HPPH-thymidine conjugate of Example 1 in the present invention.

NMR was as shown in FIG. 2, $^1$HNMR (CDCl$_3$; 400 MHz): δ 9.81, 9.79 (each peak for ½ proton, H-5), 9.40 (s, 1H, H-10), 8.53 (s, 1H, H-15), 8.46 (s, 1H, ArH), 7.18-6.89 (m, 3H,

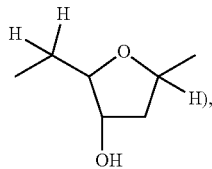

5.89 (q, J=6.5 Hz, 1H, 3$^1$-H), 5.25 (d, J=17.5 Hz, 1H, 13$^2$-CH$_2$), 5.07 (d, J=17.5 Hz, 1H, 13$^2$-CH$_2$), 4.52-4.41 (m, 1H, 18H), 4.34-4.26 (m, 1H, 17H), 4.14-4.00 (m, 1H,

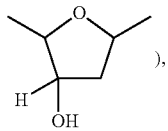

3.97-3.83 (m, 1H,

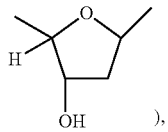

3.71-3.49 (m, 7H, 2H for 3$^1$-OCH$_2$(CH$_2$)$_4$CH$_3$, 2H for 8-CH$_2$CH$_3$, 3H for 7-CH$_3$), 3.36 (s, 3H, 2-CH$_3$), 3.23 (s, 3H, 12-CH$_3$), 2.73-2.63 (m, 1H, 17$^1$-H), 2.62-2.51 (m, 1H, 17$^1$-H), 2.38-2.26 (m, 2H,

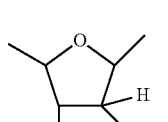

2.19-2.13 (m, 2H, 172-H), 2.09 (d, J=6.5 Hz, 3H, 3$^2$-CH$_3$), 1.78 (d, J=7.5 Hz, 3H, 18-CH$_3$), 1.70-1.57 (m, 8H, 3H for 8-CH$_2$CH$_3$, 3H for Ar—CH$_3$, 2H for 3$^1$-OCH$_2$CH$_2$(CH$_2$)$_3$CH$_3$), 1.39-1.30 (m, 6H, 3$^1$-O(CH$_2$)$_2$(CH$_2$)$_3$CH$_3$), 0.77 (t, J=10 Hz, 3H, 3$^1$-OCH$_2$(CH$_2$)$_4$CH$_3$). Mass calcd for C$_{49}$H$_{60}$N$_6$O$_8$: 860.4. found: 861.7 (MH), 883.6 (M+Na).

Example 2: Preparation of Substituted Phenyl-Containing Targeting Thymidine Kinase Photosensitizer The synthetic route and specific preparation method of the substituted phenyl-containing targeting thymidine kinase photosensitizer, i.e., 17$^3$-thymidylyl-20-(4-thymidylyloxy-carbonyl)phenyl-3-((1'-n-hexyloxy)ethyl)-3-devinyl-pyro pheophorbide, are shown below (numbered as Compound 6 in the present invention):

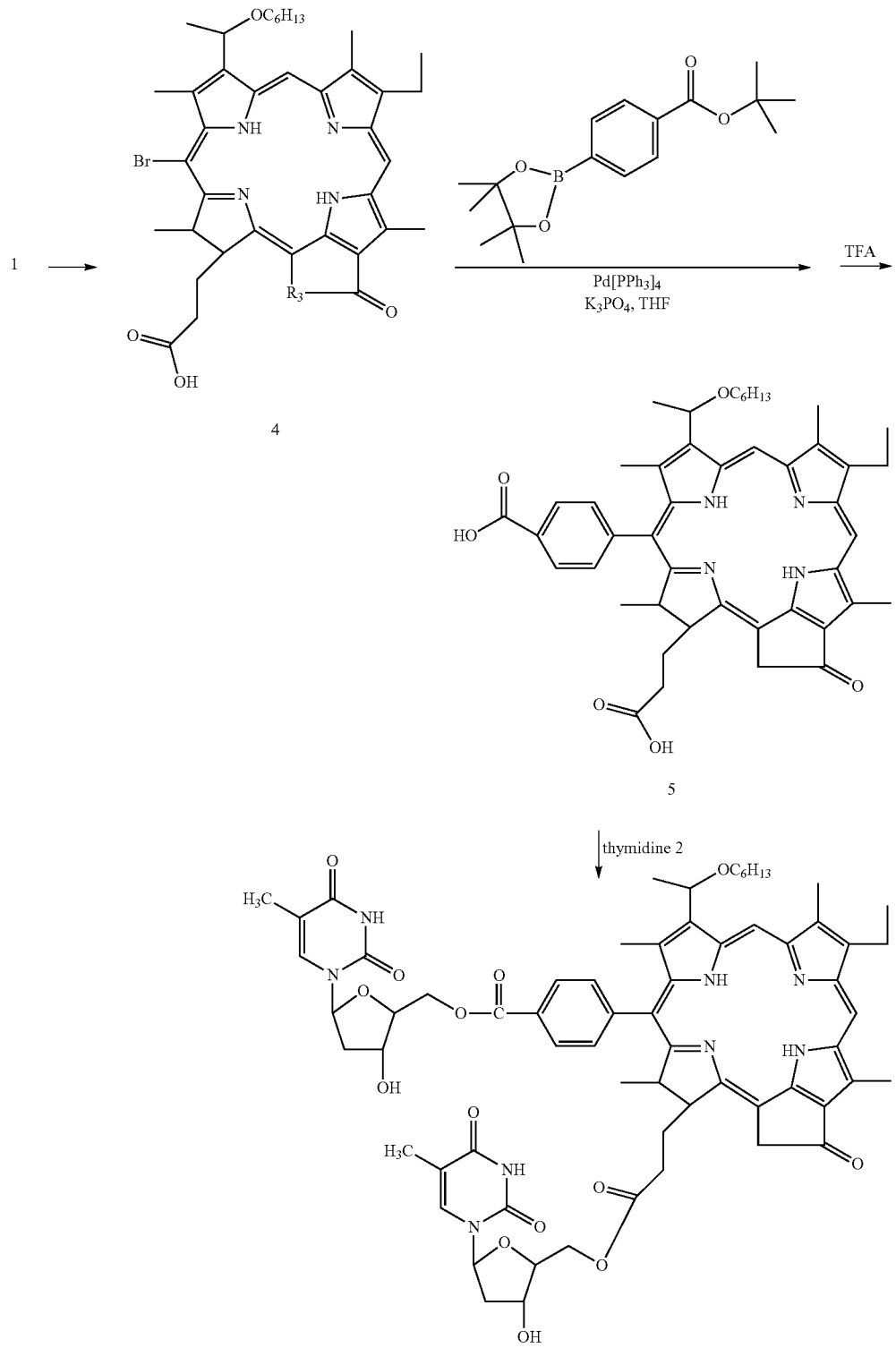

Step 1. Preparation of Compound 4:

HPPH 1 (300 mg, 0.47 mmol) and pyridinium tribromide (196 mg, 0.61 mmol) were dissolved in 10 mL dichloromethane. Subsequently, 3 drops of pyridine was added to the reaction mixture. The reaction mixture was stirred for 40 min. Thereafter, the mixture was purified by chromatography using 5% MeOH/CH$_2$Cl$_2$ as the eluent. The target compound was obtained with the yield of 48% (160 mg). UV-Visible light, $\lambda_{max}$ (CH$_2$Cl$_2$), nm ($\epsilon$): 672 nm (4.65×10$^4$), 552 nm (1.69×10$^4$), 418 nm (11.1×10$^4$). $^1$HNMR (CDCl$_3$; 400 MHz): δ 10.02 (br, s, —COOH), 7.23-6.53 (m, 2H, two meso-protons), 5.87 (br, 1H, 3$^1$-H), 5.26 (m, 1H, 13$^2$-CH$_2$), 5.09 (m, 1H, 13$^2$-CH$_2$), 4.53-4.42 (m, 1H, 18H), 4.35-4.27 (m, 1H, 17H), 3.73-3.47 (m, 7H, 2H for 3$^1$-OCH$_2$(CH$_2$)$_4$CH$_3$, 2H for 8-CH$_2$CH$_3$, 3H for 7-CH$_3$), 3.37 (m, 3H, 2-CH$_3$), 3.25 (m, 3H, 12-CH$_3$), 2.74-2.65 (m, 1H, 17$^1$-H), 2.64-2.53 (m, 1H, 17$^1$-H), 2.18-2.14 (m, 2H, 17$^2$-H), 2.10 (m, 3H, 3$^2$-CH$_3$), 1.79 (m, 3H, 18-CH$_3$), 1.71-1.58 (m, 8H, 3H for 8-CH$_2$CH$_3$, 3H for Ar-CH$_3$, 2H for 3$^1$-OCH$_2$CH$_2$(CH$_2$)$_3$CH$_3$), 1.38-1.29 (m, 6H, 3$^1$-O(CH$_2$)$_2$(CH$_2$)$_3$CH$_3$), 0.71 (m, 3H, 3$^1$-OCH$_2$(CH$_2$)$_4$CH$_3$). Mass calcd for C$_{39}$H$_{47}$BrN$_4$O$_4$: 714.3. found: 715.32 (MH).

Step 2. Preparation of Compound 5:

Compound 4 (120 mg, 0.17 mmol), 4-(t-butyloxycarboryl)phenylboronic acid pinacol ester(1551 mg, 5.1 mmol), tetrakis(triphenylphosphine)palladium(0)(79 mg, 0.068 mmol) and potassium phosphate (408 mg, 3.4 mmol) were dissolved in 50 mL dry tetrahydrofuran (THF), and the reaction mixture was refluxed for 20 h;

Thereafter, the mixture was purified by chromatography using 10% MeOH/CH$_2$Cl$_2$ as the eluent;

The compound obtained was dissolved in about 20 mL CH$_2$Cl$_2$ followed by addition of about 12 mL TFA. The mixture was stirred under argon atmosphere for 2 h, and subsequently purified by chromatography using 10% MeOH/CH$_2$Cl$_2$ to give the target compound 5 with the yield of 40% (51.5 mg).

UV-Visible light, $\lambda_{max}$ (CHCl$_3$), nm ($\epsilon$): 670 nm (4.45×10$^4$), 551 nm (1.61×10$^4$), 416 nm (10.5×10$^4$).

$^1$HNMR (CDCl$_3$; 400 MHz): δ 9.51 (br, s, —COOH), 7.89 (m, 2H, two meso-protons), 7.04 (m, 2H, Ar—H), 6.82 (m, 2H, Ar—H), 5.81 (br, 1H, 3$^1$-H), 5.28 (m, 1H, 13$^2$-CH$_2$), 5.11 (m, 1H, 13$^2$-CH$_2$), 4.53-4.44 (m, 1H, 18H), 4.36-4.27 (m, 1H, 17H), 3.74-3.46 (m, 7H, 2H for 3$^1$-OCH$_2$(CH$_2$)$_4$CH$_3$, 2H for 8-CH$_2$CH$_3$, 3H for 7-CH$_3$), 3.39 (m, 3H, 2-CH$_3$), 3.24 (m, 3H, 12-CH$_3$), 2.75-2.67 (m, 1H, 17$^1$-H), 2.65-2.52 (m, 1H, 17$^1$-H), 2.20-2.16 (m, 2H, 17$^2$-H), 2.11 (m, 3H, 3$^2$-CH$_3$), 1.77 (m, 3H, 18-CH$_3$), 1.72-1.59 (m, 8H, 3H for 8-CH$_2$CH$_3$, 3H for Ar-CH$_3$, 2H for 3$^1$-OCH$_2$CH$_2$(CH$_2$)$_3$CH$_3$), 1.37-1.27 (m, 6H, 3$^1$-O(CH$_2$)$_2$(CH$_2$)$_3$CH$_3$), 0.74 (m, 3H, 3$^1$-OCH$_2$(CH$_2$)$_4$CH$_3$). Mass calcd for C$_{46}$H$_{52}$N$_4$O$_6$: 756.4. found: 756.75.

Step 3. Preparation of Compound 6:

Compound 5 (112 mg, 0.148 mmol), BOP (408 mg, 0.92 mmol), thymidine (2520 mg, 10.36 mmol) and triethylamine (about 1.0 mL) were dissolved in about 15 mL anhydrous DMF, and stirred over night. After removal of DMF under high vacuum, the mixture was purified by chromatography using 5% MeOH/CH$_2$Cl$_2$ as the eluent to give the target compound with the yield of 41% (73 mg). UV-Visible light, $\lambda_{max}$ (CHCl$_3$), nm ($\epsilon$): 671 nm (4.46×10$^4$), 553 nm (1.63×10$^4$), 416 nm (10.7×10$^4$). $^1$HNMR (CDCl$_3$; 400 MHz): 8.46 (m, 2H, 2×ArH), 7.89 (m, 2H, two meso-protons), 7.18-7.05 (m, 6H, 2×

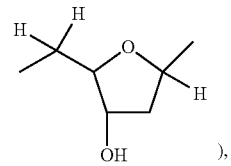

7.04 (m, 2H, Ar—H), 6.82 (m, 2H, Ar—H), 5.81 (br, 1H, 3$^1$-H), 5.28 (m, 1H, 13$^2$-CH$_2$), 5.11 (m, 1H, 13$^2$-CH$_2$), 4.53-4.44 (m, 1H, 18H), 4.36-4.27 (m, 1H, 17H), 4.14-4.00 (m, 2H, 2×

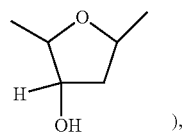

3.97-3.83 (m, 2H, 2×

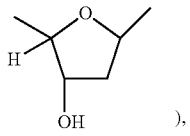

3.74-3.46 (m, 7H, 2H for 3$^1$-OCH$_2$(CH$_2$)$_4$CH$_3$, 2H for 8-CH$_2$CH$_3$, 3H for 7-CH$_3$), 3.39 (m, 3H, 2-CH$_3$), 3.24 (m, 3H, 12-CH$_3$), 2.75-2.67 (m, 1H, 17$^1$-H), 2.65-2.52 (m, 1H, 17$^1$-H), 2.38-2.26 (m, 4H, 2×

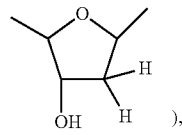

2.20-2.16 (m, 2H, 17$^2$-H), 2.11 (m, 3H, 3$^2$-CH$_3$), 1.77 (m, 3H, 18-CH$_3$), 1.72-1.59 (m, 8H, 3H for 8-CH$_2$CH$_3$, 3H for Ar-CH$_3$, 2H for 3$^1$-OCH$_2$CH$_2$(CH$_2$)$_3$CH$_3$), 1.37-1.27 (m, 6H, 3$^1$-O(CH$_2$)$_2$(CH$_2$)$_3$CH$_3$), 0.74 (m, 3H, 3$^1$-OCH$_2$(CH$_2$)$_4$CH$_3$). Mass calcd for C$_{66}$H$_{76}$N$_8$O$_{14}$: 1204.55. found: 1205.67 (MH).

Example 3: Preparation of the Targeting Thymidine Kinase Photosensitizer Containing Additional N-Heterocycle Synthetic Route:

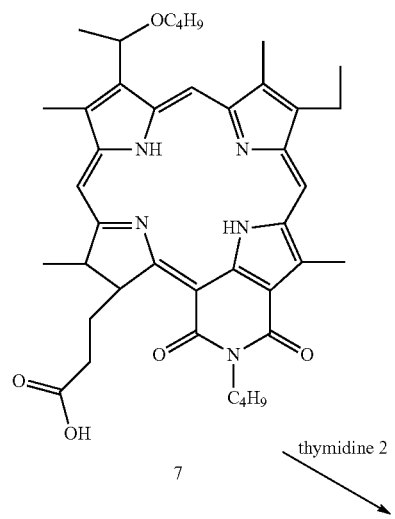

7

↓ thymidine 2

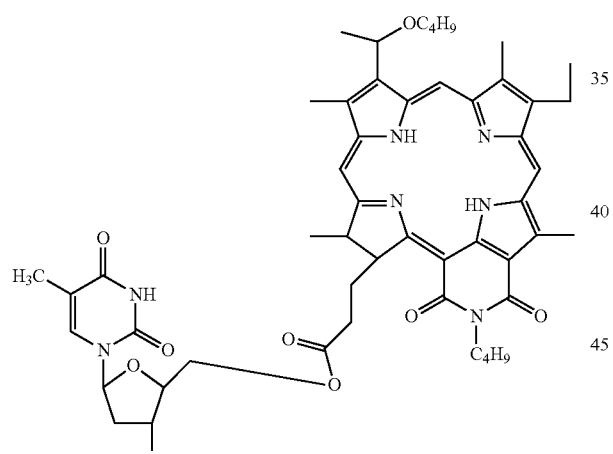

8

Specific procedure was as follows:

3-(1-(butoxy)ethyl)purpurin-18-N-butyramide-17-propanoic acid 7 (120 mg, 0.173 mmol), BOP (169 mg, 0.38 mmol), thymidine (1050 mg, 4.32 mmol) and triethylamine (about 0.5 mL) were dissolved in about 15 mL anhydrous DMF, and stirred over night. After removal of DMF under high vacuum, the mixture was purified by chromatography using 5% MeOH/CH$_2$Cl$_2$ as the eluent to give the target compound with the yield of 51% (80 mg). UV-Visible light, $\lambda_{max}$ (MeOH), nm ($\epsilon$):699 nm (4.51×10$^4$), 642 (7.31×10$^3$), 543 (1.79×10$^4$), 507 (7.29×10$^3$), 413 (12.52×10$^4$). $^1$HNMR (CDCl$_3$; 400 MHz): δ 9.79, (s, 1H, H-5), 9.66 (s, 1H, H-10), 8.53 (s, 1H, H-15), 7.21 (s, 1H, ArH), 7.03 (m, 1H,

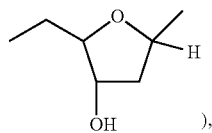

6.80 (m, 3H,

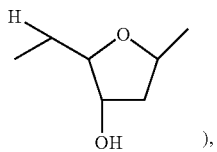

6.22 (m, 3H,

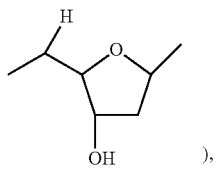

5.80 (q, J=6.5 Hz, 1H, 3$^1$-H), 5.37 (m, 2H, —NCH$_2$(CH$_2$)$_2$CH$_3$), 4.52-4.41 (m, 1H, 18H), 4.34-4.26 (m, 1H, 17H), 4.14-4.00 (m, 1H,

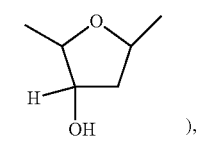

3.97-3.83 (m, 1H,

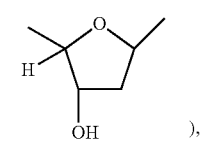

3.71-3.49 (m, 7H, 2H for 3$^1$-OCH$_2$(CH$_2$)$_2$CH$_3$, 2H for 8-CH$_2$CH$_3$, 3H for 7-CH$_3$), 3.35 (s, 3H, 2-CH$_3$), 3.23 (s, 3H, 12-CH$_3$), 2.73-2.63 (m, 1H, 17$^1$-H), 2.62-2.51 (m, 1H, 17'-H), 2.38-2.26 (m, 2H,

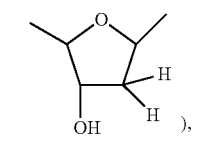

2.19-2.13 (m, 2H, 17$^2$-H), 2.09 (d, J=6.5 Hz, 3H, 3$^2$-CH$_3$), 1.78 (d, J=7.5 Hz, 3H, 18-CH$_3$), 1.70-1.57 (m, 8H, 3H for 8-CH$_2$CH$_3$, 3H for Ar-CH$_3$, 2H for 3$^1$-OCH$_2$(CH$_2$)$_2$CH$_3$), 1.39-1.30 (m, 6H, 3$^1$-O(CH$_2$)$_2$(CH$_2$)$_2$CH$_3$), 1.07 (t, J=10

Hz, 3H, —NCH$_2$(CH$_2$)$_2$CH$_3$), 0.88 (t, J=9.8 Hz, 3H, 3$^1$-OCH$_2$(CH$_2$)$_4$CH$_3$). Mass calcd for: C$_{51}$H$_{63}$N$_7$O$_9$: 917.47. Found: 918.5 (MH).

Example 4: Comparison of In Vitro Therapeutic Effect of PDT Among HPPH, HPPH-Thymidine Conjugate and HPPH-Thymidine Conjugate in Combination with Chemotherapeutic Agent Paclitaxel In the present invention, the in vitro therapeutic effect of PDT was compared among HPPH, HPPH-thymidine conjugate and HPPH-thymidine conjugate in combination with chemotherapeutic agent paclitaxel in an in vitro light-induced cytotoxicity test.

Procedure: in this Example, a highly metastatic and androgen-dependent prostatic cancer cell, PC3 cell line, was selected. The PC3 cells were cultured in RPMI 1640 medium supplemented with 10% fetal bovine serum, L-glutamine, penicillin, and streptomycin at 37° C., 5% CO$_2$ and 95% air, and 100% humidity. Subsequently, the PC3 cells were inoculated in the complete medium in a 96-well plate at the density of 5×10$^3$ cell/well with 6 multiple wells arranged. After cultured at 37° C. overnight, the cells were treated by the photosensitizer or paclitaxel at gradient concentrations in darkness for 24 h. For the treatment using HPPH-thymidine conjugate in combination with paclitaxel, paclitaxel was additionally injected 8 h before exposure, and the concentrations of paclitaxel and the photosensitizer were the same as above.

After the pharmaceutical-containing medium was replaced by fresh medium, the cells were irradiated by light at 665 nm and with a dosage rate of 3.2 mW/cm$^2$ using an argon-pumped dye laser.

After treated by PDT or paclitaxel alone, the cells were cultured for 48 h at 37° C. in darkness. The phototoxicity was determined by MTT assay (by comparison of the survival rate between the test cells and the untreated cells). The dosage-response survival curve was also plotted. In the Figures, the value was the average of 3 independent experiments, and the error bar stood for standard deviation. The statistical experimental results were shown in FIG. 3. In each treatment, the concentration of Compound 3, i.e., HPPH-thymidine conjugate, was 0.06 μM, and the concentration of Compound 1, i.e., HPPH, was 0.06 μM, and the concentration of paclitaxel was 2 nM.

Figure 3:
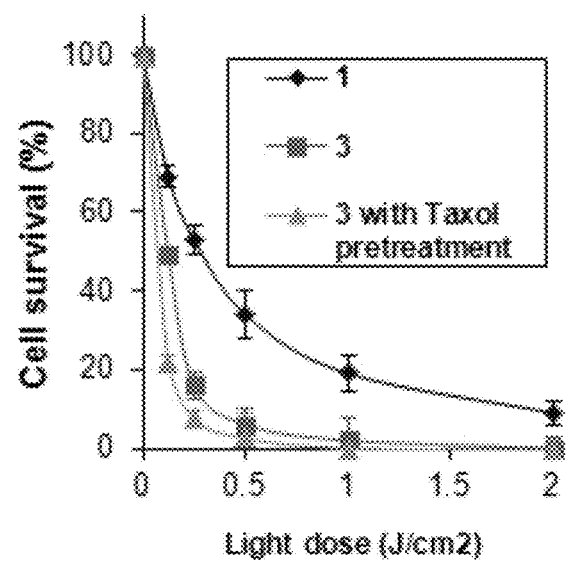
FIG. 3 is a diagram showing the comparison of the in vitro therapeutic effect of PDT using HPPH, HPPH-thymidine conjugate and HPPH-thymidine conjugate in combination with paclitaxel in Example 4, wherein the X axis is the light dosage (expressed in $J/CM^2$); and the Y axis is the cell survival (%); Compound 1 refers to HPPH; Compound 3 refers to the HPPH-thymidine conjugate of the present invention.

As shown in FIG. 3, the therapeutic effect of PDT using HPPH-thymidine conjugate was higher than that using HPPH, and the therapeutic effect was further enhanced by using HPPH-thymidine conjugate in combination with paclitaxel, wherein the cells was pretreated by paclitaxel at a minimum effective dosage (2 nM), and the light dosage of IC$_{50}$ using pharmaceutical 3 (i.e., HPPH-thymidine conjugate) for PDT therapy was significantly reduced from 0.13 J/cm$^2$ to 0.067 J/cm$^2$ (p<0.001). In addition, the morphology change was also evaluated by DAPI staining method, which came to the conclusion that the cell death was induced by paclitaxel pretreatment based on the apoptosis mechanism.

In another aspect, it was found by further investigation that after pretreatment by paclitaxel, cytotoxicity of paclitaxel can be enhanced by the treatment using Pharmaceutical 3 as the photosensitizer (concentration of 0.003 μM, light dosage of 0.25 J/cm$^2$): at low pharmaceutical concentration and light dosage, cancer cells can not be destroyed by PDT itself, but the survival rate can be reduced; while under the action of paclitaxel (0.000704), the survival rate can be reduced from 100% to 80%.

Example 5: In Vitro Therapeutic Effect of PDT Using Photosensitizer of Example 2 and 3 in the Invention The in vitro therapeutic effect of PDT was compared among the following compounds in PC-3 (human prostatic cancer) cell line by in vitro light cytotoxicity test. The procedure was the same as that in Example 4. Briefly, PC3 cells were coated onto the wells of a 96-well plate and adhered for 6-24 h. Subsequently, the cells were treated by the PDT photosensitizer at various concentrations for 24 h, followed by irradiation at 675 nm (dose rate of 3.2 mW/cm$^2$) or 703 nm (dose rate of 3.2 mW/cm$^2$) using various high dosages. After 48 h, the cell growth was evaluated by colorimetry, wherein the insoluble formazan product generated in MTT method was dissolved and its concentration was detected at 570 nm through optical density.

Figure 4:
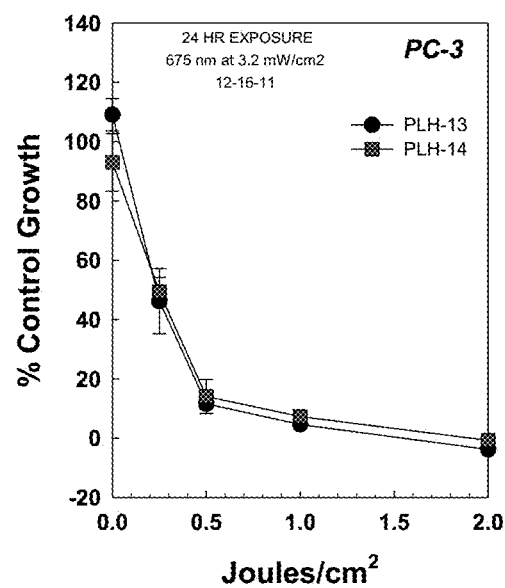
FIG. 4 is a comparing diagram showing the in vitro therapeutic effect of PDT using the photosensitizer involved in Example 2, wherein the X axis is the light dosage (expressed in J/CM$^2$); and the Y axis is the percentage of control growth (%)
Figure 5:
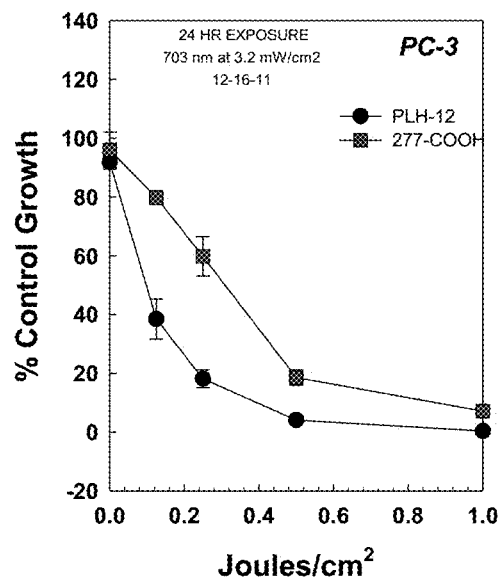
FIG. 5 is a comparing diagram showing the in vitro therapeutic effect of PDT using the photosensitizer involved in Example 3, wherein the X axis is the light dosage (expressed in J/CM$^2$); and the Y axis is relative growth rate (%)

The results of the treatment at 675 nm were shown in FIG. 4, wherein PLH-14 was Compound 5 in Example 2, and PLH-13 was Compound 6, i.e., thymidine conjugate of Compound 5, in Example 2. The concentration of both PLH-13 and PLH-14 was 0.1 μM. The results of the treatment at 703 nm were shown in FIG. 5, wherein 277-COOH was Compound 7 in Example 3, and PLH-12 was Compound 8, i.e., thymidine conjugate of Compound 7, in Example 3. The concentration of both 277-COOH and PLH-12 was 0.05 μM. As shown in FIG. 4 and FIG. 5, the in vitro therapeutic effect of PDT using the photosensitizer was enhanced by conjugation of Compound 5, Compound 6, and Compound 7 with thymidine.

Example 6: Comparison of In Vivo Therapeutic Effect of PDT Among HPPH, HPPH-Thymidine Conjugate and HPPH-Thymidine Conjugate in Combination with Paclitaxel The in vivo relative therapeutic effect of HPPH, HPPH-thymidine conjugate and HPPH-thymidine conjugate in combination with paclitaxel was determined in Scid mice possessing tumor cells of PC3 line (4×4 mm) using the method for detecting the activity of the photosensitizer in vivo.

Procedure: subcutaneous injection of 3×10$^5$ tumor cells were performed to the mice, and the cells were allowed to grow so that the diameter can reach 4-5 mm. The hairs at the inoculation site were shaved one day before laser irradiation, and the photosensitizer at various concentrations was intravenously injected to the mice. The mice were not anesthetized, and were limited in a plastic circle 24 h after photosensitizer injection (such as Compound 1 or 3). Subsequently, light treatment was performed after the emission wavelength was tuned to the activation wavelength of the drug using an argon-pumped dye laser monochromes, wherein paclitaxel was additionally injected 8 h before exposure in the combination therapy group. The parameters involved in the therapy included a diameter of 1 cm$^2$, fluence rate of 75 mW/cm$^2$ and total light dosage of 135 J/cm$^2$.

The loss of body weight, necrotic scabbing or evidence for tumor relapse was observed for the mice on each day. If tumor growth was observed, two perpendicular values L and W (perpendicular to L) were used for the detection, and the volume of tumor can be calculated according to the equation V=(L×W$^2$)/2. If no evidence for regeneration can be observed 60 days after PDT therapy, the mice can be considered as cured. There were 10 mice in each group at each concentration.

The dosages of HPPH and HPPH-thymidine conjugate used in this experiment were both 0.5 μmol/kg. The single dosage of paclitaxel for additional injection 8 h before exposure was 35 mg/kg. The irradiation parameters included 665 nm, 135 J/cm², and 75 mW/cm². The tumor relapse was monitored for a period of 60 days, and the results were shown in FIG. 6. The curative ratio can be simply calculated based on the equation: number of mice without tumor regeneration×100%/total number of mice. For example, 60 days after administration of Compound 3, i.e., HPPH-thymidine conjugate of the present invention, there were 5 mice without tumor regeneration, and there were totally 10 mice in each group. Accordingly, the curative ratio is 5×100%/10, i.e., 50%.

Figure 6:
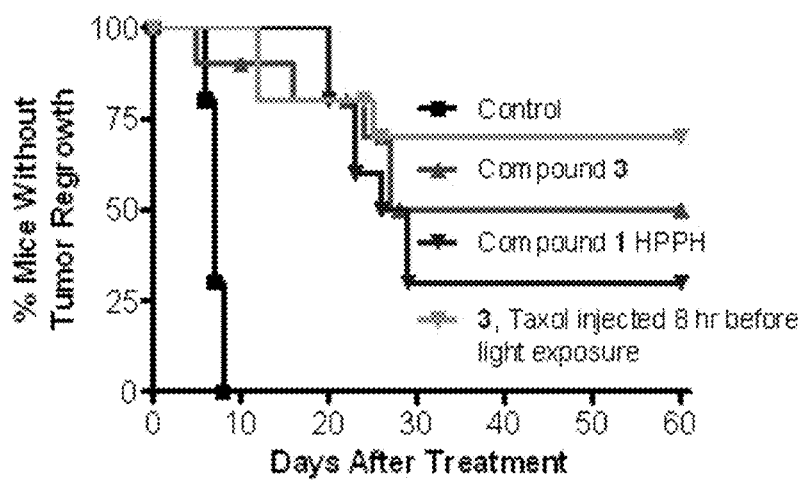
FIG. 6 is a diagram showing the comparison of the in vivo therapeutic effect of PDT using HPPH, HPPH-thymidine conjugate and HPPH-thymidine conjugate in combination with paclitaxel in Example 6; wherein Compound 1 refers to HPPH; Compound 3 refers to the HPPH-thymidine conjugate of the present invention; and wherein the X axis is the number of days after the treatment (expressed in day); and the Y axis is the curative ratio of mice (%)

As can be seen in FIG. 6, the curative ratio for HPPH was 30% (no tumor relapse observed in 3/10 mice after 60 days). As compared with HPPH, the curative ratio for the thymidine analog of equivalent amount was as high as 50% (no tumor relapse observed in 5/10 mice after 60 days). In addition, the in vivo therapeutic effect of PDT was further enhanced by HPPH-thymidine conjugate in combination with paclitaxel. Tumor disappeared in 7/10 mice after 60 days (no relapse observed).

Example 7: Fluorescence Imaging Performance of HPPH-Thymidine Conjugate

The fluorescence imaging performance of HPPH-thymidine conjugate was detected by fluorescence imaging assay.

The principle of fluorescence imaging: in vivo fluorescence imaging was achieved by a binary irradiation system (Lightools Research, Encinitas, Calif.), which was designed specially for small animals. True color fluorescence imaging was obtained by an insulated long filter (Chroma Tech) and a color digital video camera (Optronics, Magnafire SP, Olympus America). The method for wavelength resolution spectral imaging was achieved by a multi-spectral imaging system containing an optical head (CRI, Inc., Woburn, Mass.). The system included a Varispec liquid crystal tunable filter (LCTFs, band width of 20 nm, scanning wavelength in a range from 400 to 720 nm), an optical coupler and a high resolution CCD video camera, and also software for image collection and analysis. When image was captured by the camera at each fixed exposure wavelength, the wavelength will be enhanced by the tunable filter from 550 nm to 720 nm at an interval of 10 nm. 27 TIFF images generated were stored in a separate data structure, and the spectrum was formed by overlay of each pixel. The spectrum of the autofluorescent materials and the fluorescence spectrum of the photosensitizer (PS) were obtained by manually selecting appropriate region on computer. Spectral mixing segregation algorithm (supplied by CRI Company) can be used to generate a fluorescence signal separation image for pure autofluorescent material and PS. False color fluorescence reflectance (FRI) image can be obtained for all images using image analysis software Image J.

Procedure:

According to the regulation of IACUC, 50 μL 1×10⁶ Colon 26 cells (colon cancer 26 cell, to oxter on the right back side) cultured on RPMI-1640 immune serum medium were subcutaneously injected to severe combined immuno-deficient (Scid) mice, and allowed to grow to a tumor diameter of 4-5 mm. The hairs at the inoculation site were shaved one day before the injection of photosensitizer PS, and images were collected after general anesthesia of the mice (by intraperitoneal injection of the mixture of ketamine and xylazine). In a black box, 540/40× nm (green light) irradiation was supplied by a optical fiber lighting equipment, and the scattered light was filtered by a long filter so that only 667 nm Stoke-shifted PS fluorescent light can be passed. Under the same condition, images were collected from the mice at 24 h and 48 h after the injection of Compound 3 (therapeutic dosage of 0.5 μmol/kg or 1 μmol/kg).

By reference to the method above, the dosage of HPPH-thymidine conjugate injected to the prostatic cancer mice (3 mice per group) was 0.5 μmol/kg in this experiment, and images of in vivo tumor cells of PC3 line were collected at 4 h, 14 h, 24 h and 48 h after injection (electronic absorption spectrum, excitation wavelength: 665 nm, emission wavelength: 710-720 nm). The results were shown in FIG. 7.

Figure 7:
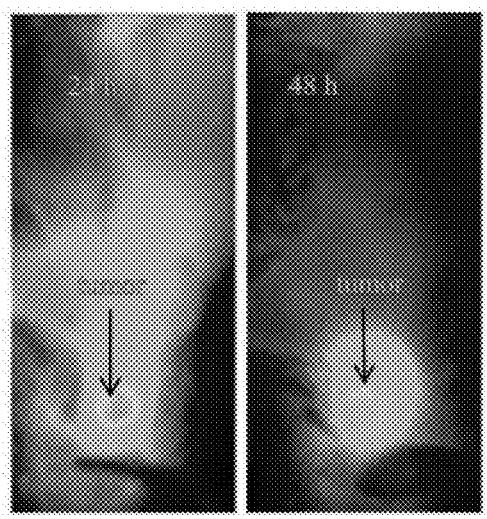
FIG. 7 is the fluorescence image diagram of the HPPH-thymidine conjugate used for tumor therapy in Example 7 of the present invention.

As shown in FIG. 7, the HPPH-thymidine conjugate described herein has a favorable imaging performance (fluorescence performance). Best adsorption/imaging quality can be obtained 24 h after the injection of the drug. The image of tumor was complete, centralized and clear. Such performance can be helpful for the imaging of prostatic cancer and other cancers, in order to assist the treatment.

The invention claimed is:

1. A targeting thymidine kinase photosensitizer, comprising the structure of Formula I:

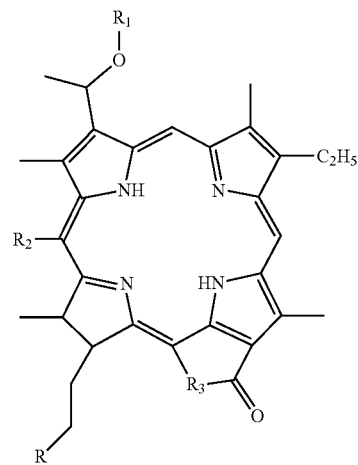

wherein, —R is —COO—$R_5$ or —CO—NH—$R_5$;

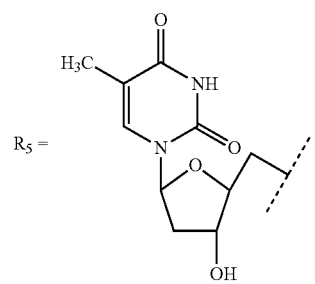

$R_5 =$ $R_1$ is alkyl;

$R_2$ is H or phenyl substituted by R at para-position, and the substituent R is defined as above;

—$R_3$ is —$CH_2$ or —CO—$NR_4$, and its carbonyl end is attached to the carbon atom of the carbon-carbon double-bond on the mother nucleus of the photosensitizer, and said $R_4$ is alkyl.

2. The photosensitizer of claim 1, wherein said R is —COO—$R_5$,

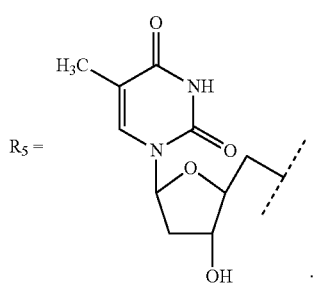

3. The photosensitizer of claim 1, wherein $R_1$ is n-butyl or n-hexyl.

4. The photosensitizer of claim 3, wherein $R_3$ is —$CH_2$ or —CO—$NR_4$, and its carbonyl end is attached to the carbon atom of the carbon-carbon double-bond on the mother nucleus of the photosensitizer, and said $R_4$ is n-butyl or n-hexyl.

5. The photosensitizer of claim 4, wherein the photosensitizer is selected from the compound represented by Formula II, Formula III or Formula IV:

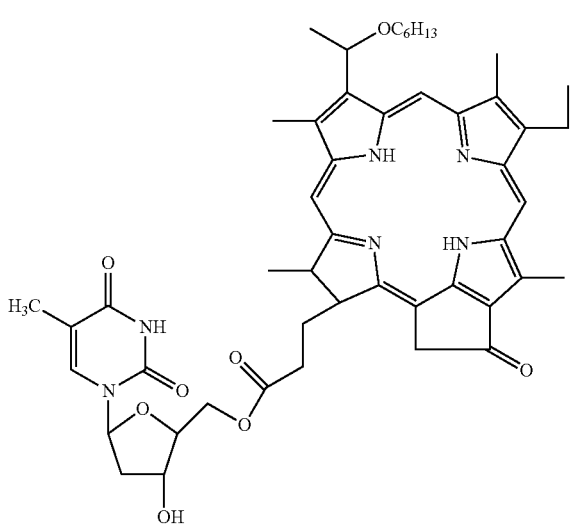

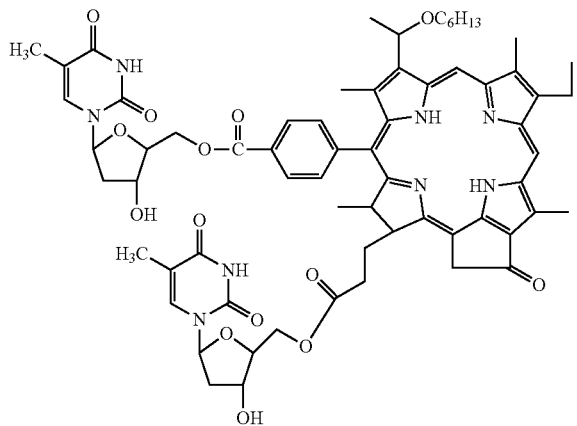

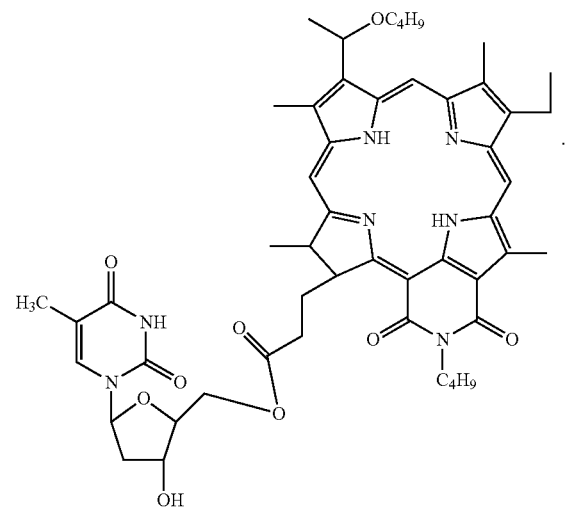

6. A method of treating prostatic cancer and other cancers via the guidance of fluorescence imaging comprising the step of administering to a patient a composition comprising the photosensitizer of claim 1.

7. A pharmaceutical composition, comprising the photosensitizer of claim 1 and a chemotherapeutic agent.

8. The pharmaceutical composition of claim 7, wherein the chemotherapeutic agent is paclitaxel.

9. A method of treating primary prostatic cancer, other primary tumors and metastatic tumors via the guidance of fluorescence imaging comprising the step of administering to a patient the composition of claim 7.

10. The method of claim 9 wherein the chemotherapeutic agent in the composition is paclitaxel.

11. The photosensitizer of claim 2, wherein $R_1$ is n-butyl or n-hexyl.

12. The photosensitizer of claim 11, wherein $R_3$ is —$CH_2$ or —CO—$NR_4$, and its carbonyl end is attached to the carbon atom of the carbon-carbon double-bond on the mother nucleus of the photosensitizer, and said $R_4$ is n-butyl or n-hexyl.

13. The photosensitizer of claim 12, wherein the photosensitizer is selected from the compound represented by Formula II, Formula III or Formula IV:

II

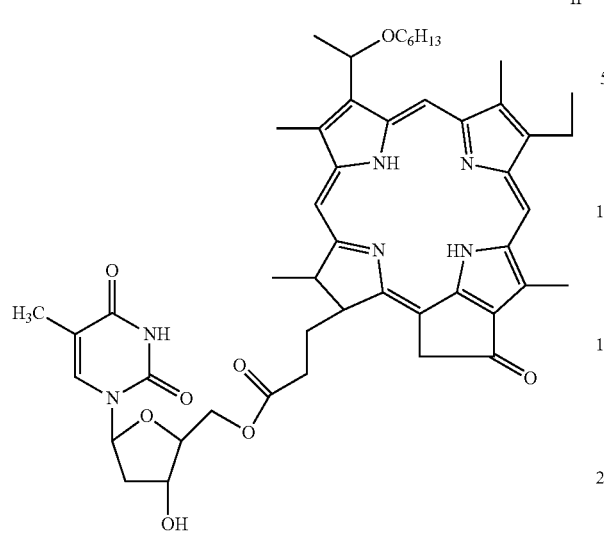

IV

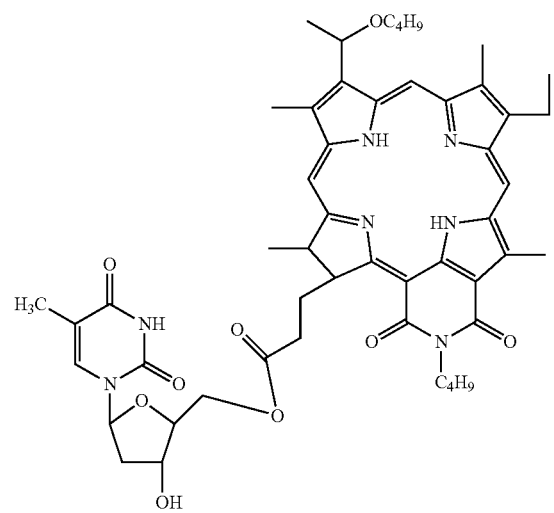

III

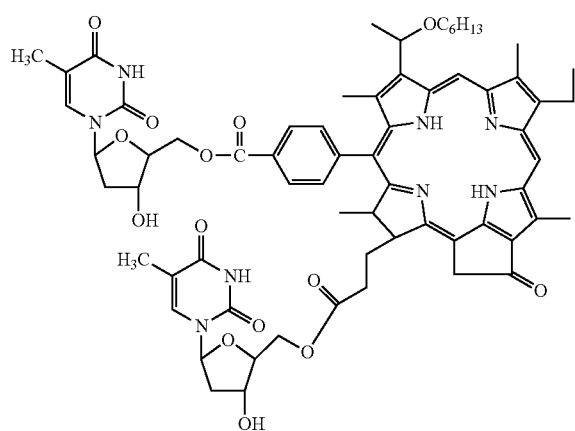

14. A method of treating prostatic cancer and other cancers via the guidance of fluorescence imaging comprising the step of administering to a patient a composition comprising the photosensitizer of claim 11.

15. A pharmaceutical composition, wherein the pharmaceutical composition comprises the photosensitizer of claim 11 and a chemotherapeutic agent.

16. The pharmaceutical composition of claim 15, wherein the chemotherapeutic agent is paclitaxel.

17. A method of treating primary prostatic cancer, other primary tumors and metastatic tumors via the guidance of fluorescence imaging comprising the step of administering to a patient the composition of claim 15.

18. The method of claim 17 wherein the chemotherapeutic agent in the composition is paclitaxel.

* * * * *